United States Patent
Ma et al.

(10) Patent No.: US 10,947,119 B2
(45) Date of Patent: Mar. 16, 2021

(54) METAL HALIDE CRYSTALS HAVING A NANOTUBE STRUCTURE AND METHODS

(71) Applicant: Florida State University Research Foundation, Inc., Tallahassee, FL (US)

(72) Inventors: Biwu Ma, Tallahassee, FL (US); Haoran Lin, Tallahassee, FL (US)

(73) Assignee: Florida State University Research Foundation, Inc., Tallahasee, FL (US)

( * ) Notice: Subject to any disclaimer, the term of this patent is extended or adjusted under 35 U.S.C. 154(b) by 186 days.

(21) Appl. No.: 16/155,231

(22) Filed: Oct. 9, 2018

(65) Prior Publication Data

US 2019/0106325 A1    Apr. 11, 2019

Related U.S. Application Data

(60) Provisional application No. 62/570,227, filed on Oct. 10, 2017.

(51) Int. Cl.

| | |
|---|---|
| *C01B 32/174* | (2017.01) |
| *H01L 51/00* | (2006.01) |
| *C07C 209/24* | (2006.01) |
| *B01J 35/00* | (2006.01) |
| *C07C 45/50* | (2006.01) |
| *B01J 31/22* | (2006.01) |
| *C07D 487/20* | (2006.01) |
| *B82Y 30/00* | (2011.01) |

(52) U.S. Cl.
CPC ............ *C01B 32/174* (2017.08); *B01J 31/22* (2013.01); *B01J 35/004* (2013.01); *B82Y 30/00* (2013.01); *C07C 45/50* (2013.01); *C07C 209/24* (2013.01); *C07D 487/20* (2013.01); *H01L 51/005* (2013.01); *H01L 51/0049* (2013.01); *Y10T 428/2913* (2015.01); *Y10T 428/2918* (2015.01); *Y10T 428/2975* (2015.01)

(58) Field of Classification Search
CPC ....... C01B 32/174; B01J 31/22; B01J 35/004; C07C 45/50; C07C 209/24; C07D 487/20; H01L 51/0049; H01L 51/005; B82Y 20/00; B82Y 30/00; B82Y 40/00; Y10T 428/2918; Y10T 428/2913; Y10T 428/2975
USPC ........ 977/762, 810, 932; 428/357, 364, 397, 428/398, 401
See application file for complete search history.

(56) References Cited

U.S. PATENT DOCUMENTS

| | | | |
|---|---|---|---|
| 2017/0217785 A1* | 8/2017 | Yang | ................. H01L 21/02422 |
| 2017/0260125 A1* | 9/2017 | Kanno | ................. H01G 9/2009 |
| 2017/0283693 A1* | 10/2017 | Ma | ......................... C09K 11/06 |

OTHER PUBLICATIONS

Wu et al., "Broad-Band-Emissive Organic-Inorganic Hybrid Semiconducting Nanowires Based on an ABX3-Type Chain Compound," Inorganic Chemistry, Jul. 10, 2017. (Year: 2017).*
Lin, et al. "Bulk assembly of organic metal halide nanotubes," Chem. Sci., Oct. 16, 2017, 8, 8400. (Year: 2017).*

(Continued)

*Primary Examiner* — Matthew D Matzek
(74) *Attorney, Agent, or Firm* — Eversheds Sutherland (US) LLP (57) ABSTRACT

Provided are organic metal halide crystals having a 1D nanotube structure. The metal halide crystals may have a unit cell that includes two or more face-sharing metal halide dimers. The metal halide crystals also may include organic cations. Methods of forming metal halide crystals having a 1D nanotube structure also are provided.

20 Claims, 8 Drawing Sheets

(56) References Cited

OTHER PUBLICATIONS

Berry et al., "Hybrid Organic-Inorganic Perovskites (HOIPs): Opportunities and Challenges," Adv. Mater., 2015 (11 pages).
Huo et al., "Two-Dimensional Metal Halide Perovskites: Theory, Synthesis, and Optoelectronics," Small Methods, 2017, 1600018 (13 pages).
Manser et al., "Intriguing Optoelectronic Properties of Metal Halide Perovskites," Chem. Rev., 2016, 116:12956-13008.
Mitzi, "Templating and Structural Engineering in Organic-Inorganic Perovskites," J. Chem. Soc., 2001, pp. 1-12.
Saparov et al., "Organic-Inorganic Perovskites: Structural Versatility for Functional Materials Design," Chem. Rev., 2016, 4558-4596.
Wang et al., "Synthesis and Characterization of [NH2C(I)=NH2]3MI5 (M=Sn, Pb): Stereochemical Activity in Divalent Tin and Lead Halides Containing Single <110> Perovskite Sheets," J. Am. Chem. Soc., 1995, 117:5297-5302.
Yuan et al., "One-Dimenskional Organic Lead Halide Perovskites with Efficient Bluish White-Light Emission," Nature Communications, 2016, pp. 1-7.
Zhou et al., "Highly Luminescent Bulk Quantum Materials Based on Zero-Dimensional Organic Tin Halide Perovskites," arXiv, 2017, 1702.07200.

\* cited by examiner

Deformation Coordinate(a.μ.)

METAL HALIDE CRYSTALS HAVING A NANOTUBE STRUCTURE AND METHODS

CROSS-REFERENCE TO RELATED APPLICATIONS

This application claims priority to U.S. Provisional Patent Application No. 62/570,227, filed Oct. 10, 2017, which is incorporated herein by reference.

BACKGROUND

Since the discovery of carbon nanotubes, materials with tubular structures have attracted interest because of their intriguing physical and/or chemical properties. Besides carbon nanotubes, a number of synthetic tubular structures, such as metal oxides, polymers, and metal organic frameworks (MOFs), have been developed.

Organic-inorganic metal halide hybrids can have exceptional optical and/or electronic properties, which makes them suitable for use in a variety of optoelectronic devices, including photovoltaic cells, light emitting diodes, photodetectors, and lasers. The structural tunability of this class of materials can enable the formation of various types of crystal structures by using appropriate organic and inorganic components. The crystal structures can range from three- (3D), to two- (2D), one- (1D), and zero-dimensional (0D) structures on the molecular level.

In the 3D structure, small size cations, such as $Cs^+$ and $CH_3NH_3^+$, may fit into corner-sharing metal halide octahedrons ($MX_6$) to form a framework with the 3D $MX_6$ network. In the 2D structure, $MX_6$ octahedrons may be connected in layered or corrugated sheets at the corners. In the 1D structure, $MX_6$ octahedrons may be connected in a chain. In the 0D structure, $MX_6$ octahedrons or assemblies of octahedrons may be isolated from each other and surrounded by organic cations. These 2D, 1D, and 0D hybrids can be considered bulk assemblies of core-shell quantum confined materials, with 2D wells, 1D wires, and 0D individual metal halide octahedrons confined by organic ligands.

The isolation between the building blocks in these low dimensional metal halide hybrids can enable the bulk materials to exhibit one or more intrinsic properties of individual building blocks. In other words, organic metal halide hybrids may enable the properties of conventional individual nanostructures to be present in single crystalline bulk assemblies with defined periodicities.

There remains a need for crystal structures, including metal halide-based crystal structures, that have or include a tubular structure, including a 1D nanotube structure. There also remains a need for facile methods, such as solution processing, for making crystal structures having a tubular structure, such as a 1D nanotube structure.

BRIEF SUMMARY

Provided herein are organic metal halide crystals having a 1D tubular structure, and facile solution processing methods for preparing the metal halide crystals. The metal halide crystals provided herein may include an array of 1D nanotube structures.

In one aspect, metal halide crystals are provided. In some embodiments, the metal halide crystals have a 1D nanotube structure, and a unit cell according to formula (I)—

$$R^d_a M^c_2 X_b \quad (I);$$

wherein R is an organic cation including at least one positively charged moiety; a is 2 to 8; M is a metal atom selected from the group consisting of Sn, Pb, Sb, Bi, Ag, Au, Pd, Pt, Mn, Fe, Co, Ni, Cu, and Zn; c is the charge of the metal atom; d is the charge of the organic cation; X is a halide ion selected from the group consisting of Cl, Br, and I; b is 5 to 12; and the selections for a, b, c, and d satisfy the following equation: 2(c)+a(d)=b.

In some embodiments, the metal halide crystals have a 1D nanotube structure, and a unit cell according to the following formula:

$$(C_6H_{13}N_4)_3Pb_2Br_7.$$

In another aspect, methods of making metal halide crystals having 1D nanotube structures are provided. In some embodiments, the methods include providing a liquid including a metal halide and an organic halide salt; and contacting the liquid with a crystallizing agent; wherein the metal halide includes a compound according to formula (II)—

$$MX_e \quad (II);$$

wherein M is a metal atom selected from the group consisting of Sn, Pb, Sb, Bi, Ag, Au, Pd, Pt, Mn, Fe, Co, Ni, Cu, and Zn; X is a halide ion selected from the group consisting of Cl, Br, and I; and e is 1, 2, or 3.

DETAILED DESCRIPTION

The unique nanotubular structure of embodiments of the metal halide crystals described herein may be advantageous in a number of potential applications, including, but not limited to, gas storage, ion selection, etc. Not wishing to be bound by any particular theory, it is believed that the use of an organic cation, such as protonated hexamethylenetetramine (HMTA) ($C_6H_{13}N_4^+$), can dictate the assembly of metal halides, thereby resulting, in some embodiments, in a bulk assembly of 1D metal halide nanotubes, such as those having a chemical formula of $(C_6H_{13}N_4)_3Pb_2Br_7$.

It is believed that due to the complete isolation and/or strong quantum confinement of individual metal halide nanotubes by wide band gap organic moieties in some embodiments, the nanotube-assembled materials having a 1D structure provided herein can exhibit one or more intrinsic properties of the individual metal halide nanotubes. In some embodiments, strongly Stokes shifted broadband yellowish white emission peaks at about 580 nm with a large full width at half maximum (FWHM) of about 158 nm. In some embodiments, the metal halide crystals have a photoluminescence quantum efficiency of about 7%, likely due to exciton self-trapping in the metal halide frameworks.

Metal Halide Crystals

Metal halide crystals are provided herein. In some embodiments, the metal halide crystals have a 1D nanotube structure, and a unit cell according to formula (I)—

$$R^d{}_a M^c{}_2 X_b \qquad (I);$$

wherein R is an organic cation including at least one positively charged moiety; a is 2 to 8; M is a metal atom selected from the group consisting of Sn, Pb, Sb, Bi, Ag, Au, Pd, Pt, Mn, Fe, Co, Ni, Cu, and Zn; c is the charge of the metal atom; d is the charge of the organic cation; X is a halide ion selected from the group consisting of Cl, Br, and I; b is 5 to 12; and the selections for a, b, c, and d satisfy the following equation: 2(c)+a(d)=b. This equation ensures that the charges of formula (I) are balanced.

In some embodiments, the metal halide crystals provided herein have a 1D nanotube structure. As used herein, the phrases "1D nanotube structure", "1D tubular structure", "nanotube structure", and the like refer to crystals in which a number (e.g., three to eight) metal halides (e.g., face-sharing metal halide dimers, such as $Pb_2Br_7^{3-}$) form a "ring", and a plurality of these "rings" substantially align and extend in one dimension, thereby forming a metal halide tube having an outer portion and an inner portion defined by the "rings". The 1D nanotube structures may include one or more metal halide nanotubes formed in this manner. Organic cations, such as protonated hexamethylenetetramine (HMTA) cations ($C_6H_{13}N_4^+$), may be located at the inner portion and/or the outer portion of the metal halide tube(s). The "rings" formed by the metal halides may define a space that is substantially circular, but other shapes (e.g., oval, polygonal (e.g., hexagonal, octagonal, etc.), rectangular, star-shaped, etc.) are possible. The metal halides of the "rings" may be connected at one or more positions (e.g., at corners of the "rings" like the face-sharing metal halide dimers of formula $Pb_2Br_7^{3-}$).

Figure 1:
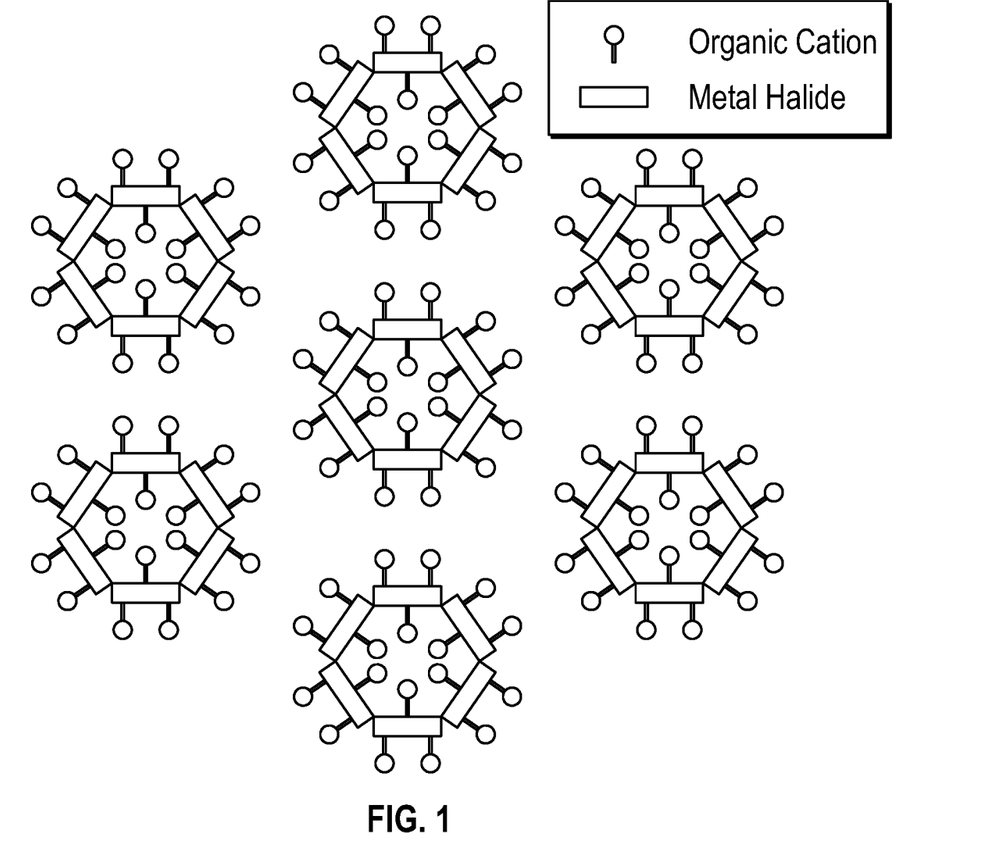
FIG. 1 depicts a schematic of an embodiment of a 1D nanotube crystal.

In some embodiments, the 1D nanotube structure includes a single-wall structure (e.g., as depicted at FIG. 1), a multiple-wall structure, or a combination thereof. A multiple-wall structure may include two or more concentric "rings" of metal halides that form two or more concentric metal halide tubes.

In some embodiments, the rings of the 1D nanotube structures include three or more metal halide units. In some embodiments, the rings of the 1D nanotube structures include three to eight metal halide units. In some embodiments, the rings of the 1D nanotube structures include four to eight metal halide units. In some embodiments, the rings of the 1D nanotube structures include six metal halide units.

An embodiment of a 1D nanotube structure is depicted at FIG. 1. FIG. 1 is a schematic depicting a cross-sectional view of an embodiment of a metal halide crystal having a 1D nanotube structure in which six, face-sharing metal halides form rings, which can extend in one dimension to form tubes. The rings define an inner portion and an outer portion at which the organic cations are located. The metal halides of FIG. 1 are represented by the rectangles, and the organic cations are represented by the circles. The ratio of the number of organic cations located at the inner portion of the tube to the outer portion of the tube is about 1:2 in FIG. 1. The dashes of FIG. 1 may represent at least one force, such as an attractive force, between an organic cation and a metal halide. The force represented by each dash may result from the one or more positively charged moieties of an organic cation. The 1D nanotube structure of FIG. 1 includes an array of nanotube structures in a hexagonal close-packed pattern, but other packing patterns are possible.

The metal halide crystals provided herein generally may emit any color of light. The metal halide crystals may emit light in response to photo-excitation. In some embodiments, the metal halide crystals emit yellowish-white light. In some embodiments, the metal halide crystals emit white light. In some embodiments, the metal halide crystals have a photoluminescence quantum efficiency (PLQE) of about 3%, about 4%, about 5%, about 5%, about 7%, about 8%, about 9%, or about 10%. In some embodiments, the metal halide crystals have a PLQE of about 3% to about 10%.

Organic Cations

Any organic cation that includes at least one positively charged moiety may be included the metal halide crystals provided herein, or used in the methods provided herein. In some embodiments, the organic cation includes one positively charged moiety. In some embodiments, the organic cation includes two positively charged moieties. In some embodiments, the organic cation includes three positively charged moieties.

In some embodiments, the organic cation is a $C_1$-$C_{24}$ hydrocarbyl that includes at least one positively charged moiety, such as a positively charged amine. In some embodiments, the organic cation is a $C_1$-$C_{24}$ hydrocarbyl that includes two to four positively charged moieties, such as two to four positively charged amines.

In some embodiments, the organic cation is a $C_1$-$C_{24}$ hydrocarbyl that includes at least one of a protonated primary amine, a protonated secondary amine, a protonated tertiary amine, a quaternary amine, or a combination thereof. In a further embodiment, the organic cation is a $C_1$-$C_{24}$ hydrocarbyl that includes one to four protonated tertiary amines.

In some embodiments, R of formula (I) is hexamethylenetetramine, and "d" of formula (I) is 1, 2, 3, or 4, as shown, respectively, in the following structures:

The positive charges are assigned arbitrarily to the nitrogen atoms in the foregoing structures, and other assignments are envisioned.

In some embodiments, the organic cation (R of formula (I)) is selected from the group consisting of N,N,N-trimethyloctan-1-aminium; tetraethylammonium; tetrabutylammonium; N,N-dimethylhexan-1-aminium; bis(2-ethylhexyl)ammonium; $N^1$-methylethane-1,2-diaminium; $N^1,N^2$-dimethylethane-1,2-diaminium; $N^1,N^1,N^2,N^2$-tetramethylethane-1,2-diaminium; $N^1,N^1$-dimethylethane-1,2-diaminium; $N^1,N^1,N^2$-trimethylethane-1,2-diaminium; 2,6-dimethylpyridin-1-ium; 2-amino-4-methylpyridin-1-ium; [4,4'-bipyridine]-1,1'-diium; [4,4'-bipyridin]-1-ium; 4-(di(pyridin-4-yl)amino)pyridin-1-ium; 1-butyl-1-methylpyrrolidin-1-ium; 3-butyl-1-methyl-1H-imidazol-3-ium; 3-(pyrrolidin-1-yl)propan-1-aminium; 2-(pyrrolidin-2-yl)ethanaminium; 1,1-dibutylpiperidin-1-ium; 5-azaspiro[4.4]nonan-5-ium; (1r,3r,5s,7s)-1,3,5,7-tetraazaadamantane-1,3-diium; 6-azaspiro[5.5]undecan-6-ium; 1,4-diazabicyclo[2.2.2]octan-1-ium; (3s,5s,7s)-1-azaadamantan-1-ium; (3r,5r,7r)-1,3,5,7-tetraazaadamantan-1-ium (i.e., protonated hexamethylenetetramine); tetraphenylphosphonium; and a combination thereof.

The foregoing compounds may be represented by the following structures:

and

The organic cations may be located at any position in the metal halide crystals provided herein. In some embodiments, the 1D nanotube structure includes a metal halide tube, as described herein, that has an inner portion and an outer portion, and the organic cations are located at the inner portion of the tube, the outer portion of the tube, or both the inner portion and the outer portion of the tube.

In some embodiments, the organic cations are located at the inner portion of the metal halide tube and the outer portion of the metal halide tube, and a ratio of the number of organic cations located at the inner portion of the tube to the outer portion of the tube is about 1:1 to about 1:5. In some embodiments, the organic cations are located at the inner portion of the metal halide tube and the outer portion of the metal halide tube, and a ratio of the number of organic cations located at the inner portion of the tube to the outer portion of the tube is about 1:1 to about 1:4. In some embodiments, the organic cations are located at the inner portion of the metal halide tube and the outer portion of the metal halide tube, and a ratio of the number of organic cations located at the inner portion of the tube to the outer portion of the tube is about 1:1 to about 1:3. In some embodiments, the organic cations are located at the inner portion of the metal halide tube and the outer portion of the metal halide tube, and a ratio of the number of organic cations located at the inner portion of the tube to the outer portion of the tube is about 1:2. The ratio may be determined by X-ray diffraction as described herein.

Metal Halides

Any metal halide capable of forming a metal halide crystal having a 1D nanotube structure may be included in the metal halide crystals provided herein, or used in the methods provided herein.

In some embodiments, the metal halide includes a dimer of formula $M_2X_9$, which may be a face-sharing dimer in the 1D nanotube structures provided herein. In some embodiments, the metal halide crystal includes two or more face-sharing lead bromide dimers of the formula $Pb_2Br_7^{3-}$. In some embodiments, the metal halide crystal includes three to eight face-sharing lead bromide dimers of the formula $Pb_2Br_7^{3-}$. In some embodiments, the metal halide crystal includes six face-sharing lead bromide dimers of the formula $Pb_2Br_7^{3-}$.

In some embodiments, the metal halide crystals have a 1D nanotube structure, and a unit cell according to formula (I)—

$$R^d_a M^c_2 X_b \quad\quad (I);$$

wherein d is 1. In some embodiments, M is Pb, and c is 2. In some embodiments, X is Br. In some embodiments, d is 1, M is Pb, and c is 2. In some embodiments, d is 1, M is Pb, c is 2, and X is Br. In some embodiments, d is 1, a is 3, M is Pb, c is 2, X is Br, b is 7, and the unit cell of the metal halide crystal has the following formula:

$$(R)_3Pb_2Br_7.$$

In some embodiments, d is 1, a is 3, M is Pb, c is 2, X is Br, b is 7, R is protonated hexamethylenetetramine, and the unit cell of the metal halide crystal has the following formula:

$$(C_6H_{13}N_4)_3Pb_2Br_7.$$

Methods

Methods of making metal halide crystals having a 1D nanotube structure are provided. In some embodiments, the methods include providing a liquid that includes a metal halide and an organic halide salt; and contacting the liquid with a crystallization agent. In some embodiments, the liquid includes dimethylformamide (DMF).

In some embodiments, the metal halide includes a compound according to formula (II):

$$MX_e \quad\quad (II);$$

wherein M is a metal atom selected from the group consisting of Sn, Pb, Sb, Bi, Ag, Au, Pd, Pt, Mn, Fe, Co, Ni, Cu, and Zn, X is a halide ion selected from the group consisting of Cl, Br, and I, and e is 1, 2, or 3. In some embodiments, M is Pb, X is Br, e is 2, and the metal halide of formula (II) is $PbBr_2$. In some embodiments, the organic cation is hexamethylenetetramine hydrobromide. In some embodiments, the crystallizing agent includes dichloromethane.

The phrase "$C_1$-$C_{24}$ hydrocarbyl", and the like, as used herein, generally refers to aliphatic, aryl, or arylalkyl groups containing 1 to 24 carbon atoms. Examples of aliphatic groups, in each instance, include, but are not limited to, an alkyl group, a cycloalkyl group, an alkenyl group, a cycloalkenyl group, an alkynyl group, an alkadienyl group, a cyclic group, and the like, and includes all substituted, unsubstituted, branched, and linear analogs or derivatives thereof, in each instance having 1 to 24 carbon atoms. Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl. Examples of aryl or arylalkyl moieties include, but are not limited to, anthracenyl, azulenyl, biphenyl, fluorenyl, indan, indenyl, naphthyl, phenanthrenyl, phenyl, 1,2,3,4-tetra-hydro-naphthalene, tolyl, xylyl, mesityl, benzyl, and the like, including any heteroatom substituted derivative thereof. Two or more $C_1$-$C_{24}$ hydrocarbyl groups may be covalently bonded together.

Unless otherwise indicated, the term "substituted," when used to describe a chemical structure or moiety, refers to a derivative of that structure or moiety wherein one or more of its hydrogen atoms is substituted with a chemical moiety or functional group such as alcohol, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), tertiary amine (such as alkylamino, arylamino, arylalkylamino), aryl, aryloxy, azo, carbamoyl (—NHC(O)O— alkyl- or —OC(O) NH-alkyl), carbamyl (e.g., $CONH_2$, as well as CONH-alkyl, CONH-aryl, and CONH-arylalkyl), carboxyl, carboxylic acid, cyano, ester, ether (e.g., methoxy, ethoxy), halo, haloalkyl (e.g., —$CCl_3$, —$CF_3$, —$C(CF_3)_3$), heteroalkyl, isocyanate, isothiocyanate, nitrile, nitro, phosphodiester, sulfide, sulfonamido (e.g., $SO_2NH_2$, $SO_2NR'R''$), sulfone, sulfonyl (including alkylsulfonyl, arylsulfonyl and arylalkylsulfonyl), sulfoxide, thiol (e.g., sulfhydryl, thioether) or urea (—NHCONH-alkyl-).

While certain aspects of conventional technologies have been discussed to facilitate disclosure of various embodiments, applicants in no way disclaim these technical aspects, and it is contemplated that the present disclosure may encompass one or more of the conventional technical aspects discussed herein.

In the descriptions provided herein, the terms "includes," "is," "containing," "having," and "comprises" are used in an open-ended fashion, and thus should be interpreted to mean "including, but not limited to." When methods and metal halide crystals are claimed or described in terms of "comprising" various components or steps, the metal halide crystals and methods can also "consist essentially of" or "consist of" the various components or steps, unless stated otherwise.

The terms "a," "an," and "the" are intended to include plural alternatives, e.g., at least one. For instance, the disclosure of "a metal halide," "an organic cation," "a metal atom", and the like, is meant to encompass one, or mixtures or combinations of more than one metal halide, organic cation, metal atom, and the like, unless otherwise specified.

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

EXAMPLES

Unless stated otherwise, the following materials were used in the examples. Lead (II) bromide, hexamethylenetetramine and hydrobromic acid (48 wt. % in $H_2O$) were purchased from Sigma-Aldrich. Dichloromethane (DCM, 99.9%) and dimethylformamide (DMF, 99.8%) were purchased from VWR. All reagents and solvents were used without further purification unless otherwise stated.

Example 1—Preparation of Hexamethylenetetramine (HMTA) Hydrobromide

Hexamethylenetetramine hydrobromide was prepared by adding a hydrobromic acid solution (0.81 mL, 7.1 mmol) into hexamethylenetetramine (1.00 g, 7.1 mmol) in 150 mL ethanol at 0° C.

The white cotton-like organic salts were obtained (1.1 g, 70% yield) after removal of the solvents under vacuum, followed by washing with a suitable amount of ethanol. The salts were dried and kept in a desiccator.

Example 2—Crystal Growth of $(C_6H_{13}N_4)_3Pb_2Br_7$ Nanotube Material

Single crystalline $(HMTA)_3Pb_2Br_7$ was prepared by slow solution diffusion of dichloromethane (DCM) into dimethylformamide (DMF) precursor solutions containing lead (II) bromide ($PbBr_2$) and hexamethylenetetramine hydrobromide ($C_6H_{13}N_4Br$).

Lead (II) bromide (100 mg, 0.272 mmol) and hexamethylenetetramine hydrobromide (90.0 mg, 0.409 mmol) were mixed at 2:3 molar ratio and dissolved in dimethylformamide (DMF) (5 mL) to form a clear precursor solution.

Bulk crystals were prepared by diffusing DCM (2 mL) into the prepared DMF solution (1 mL) at room temperature overnight.

The large colorless crystals were washed with DCM and dried under reduced pressure. The yield was calculated as about 53%. $(C_6H_{13}N_4)_3Pb_2Br_7$: Anal. Calc. C, 15.47; H, 2.81; N, 12.03. Found: C, 15.95; H, 2.92; N, 11.42.

Example 3—Analysis of Hexamethylenetetramine Hydrobromide

The products of Example 2 were characterized using the following techniques.

1. Single Crystal X-Ray Diffraction (SCXRD)

Figure 2A:
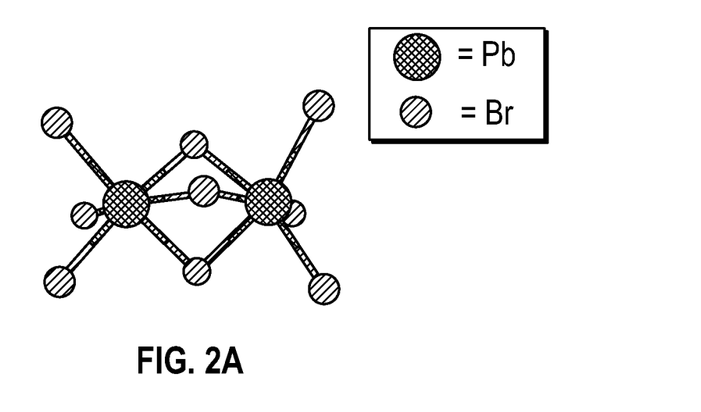
FIG. 2A depicts a ball-and-stick model of an individual face-sharing lead bromide dimer $Pb_2Br_9$.
Figure 2B:
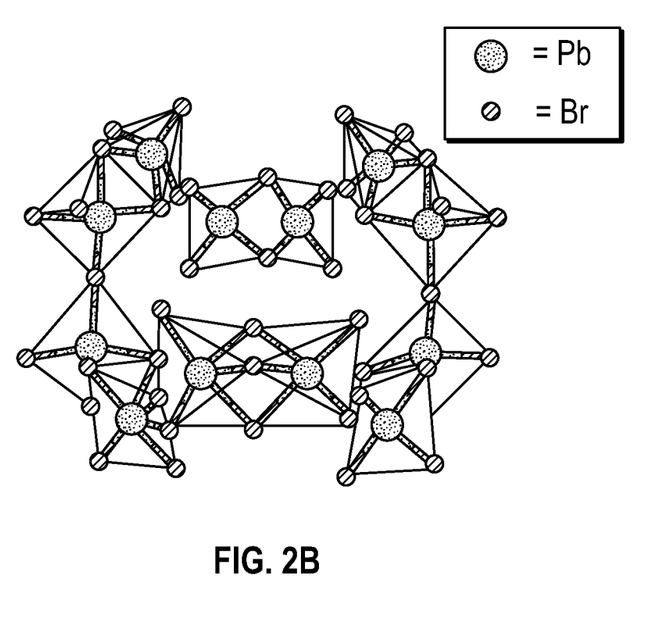
FIG. 2B depicts a rugged ring formed by six lead bromide dimers.
Figure 2C:
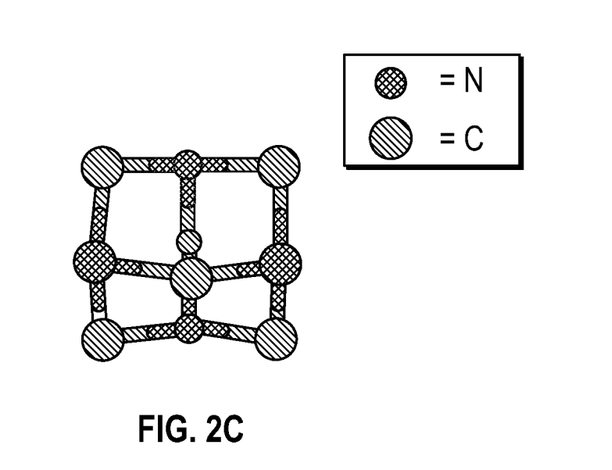
FIG. 2C depicts a ball-and-stick model of an individual hexamethylenetetramine (HMTA) $(C_6H_{13}N_4^+)$(hydrogen atoms are omitted for clarity).
Figure 2D:
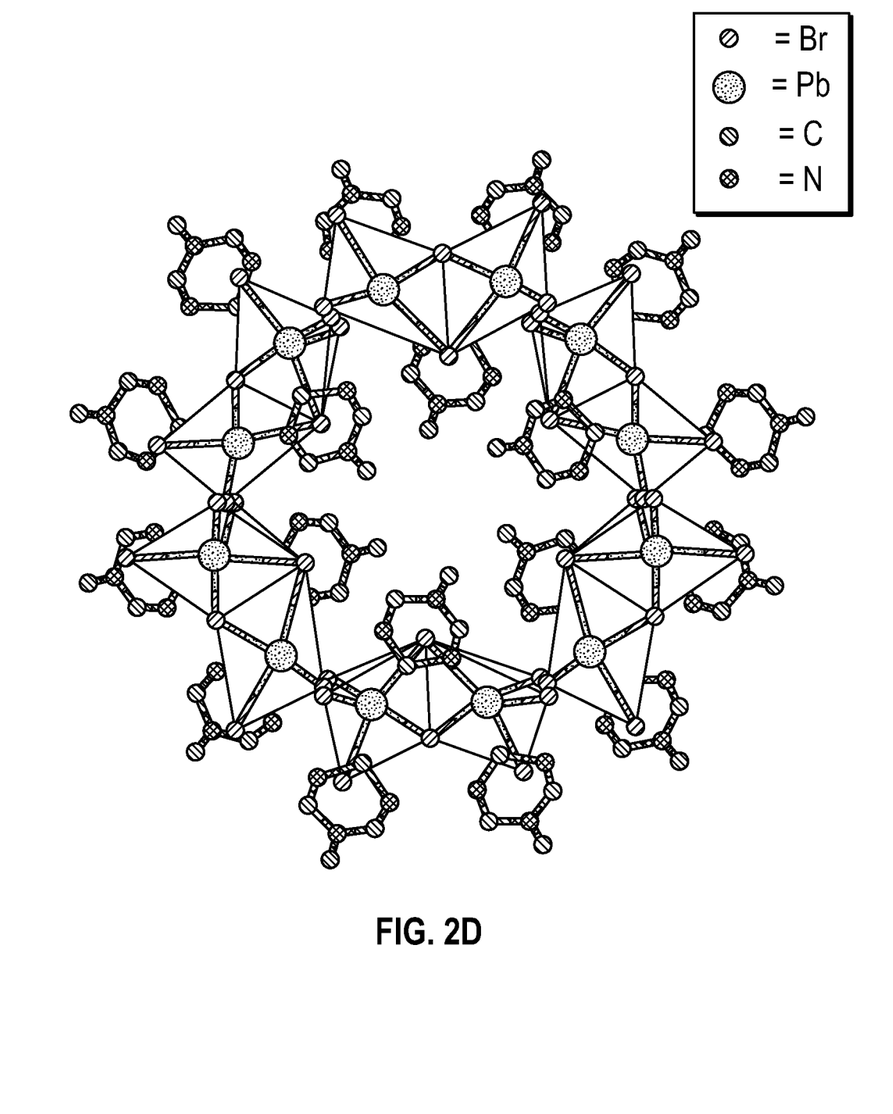
FIG. 2D depicts a view along a longitudinal axis of a nanotube, which shows HMTA cations inside and outside the nanotube.

Single crystal X-Ray Diffraction (SCXRD) was used to characterize the structure (see Tables below). Large arrays of metal halide nanotubes were observed, which included an individual nanotube surrounded by organic cations. FIG. 2A depicts a ball-and-stick model of an individual face-sharing lead bromide dimer $Pb_2Br_9$. FIG. 2B depicts a rugged ring formed by six lead bromide dimers. FIG. 2C depicts a ball-and-stick model of an individual HMTA (hydrogen atoms are omitted for clarity). FIG. 2D depicts a view along a longitudinal axis of a nanotube, which shows HMTA cations inside and outside the nanotube.

In an individual nanotube, six face-sharing lead bromide dimers $(Pb_2Br_7^{3-})$ (FIG. 2A) connected at corners to form rugged rings (FIG. 2B) with an inner radius of around 5.5 Å that extended one dimensionally.

In each "window" formed by four connected dimers on an individual hollow nanotube, three protonated HMTA cations $C_6H_{13}N_4^+$ (FIG. 2C) were anchored by columbic interaction and hydrogen bonding, with one positioned inside the tube and the other two outside (FIG. 2D). In other words, individual negatively charged metal halide nanotubes were coated by positive organic cations on both the inside and the outside at a 1/2 ratio, which resulted in an inorganic-organic core-shell nanotubular structure with an inner radius of around 3 Å taking the organic cations into account. These organic coated metal halide nanotubes further assembled into a hexagonal close packed array in a macroscopic crystal, such as the array depicted at FIG. 1.

Single crystal X-ray diffraction data of hexamethylenetetramine lead bromide $(C_6H_{13}N_4)_3Pb_2Br_7$ was collected using an Oxford-Diffraction Xcalibur-2 CCD diffractometer with graphite-monochromated Mo Kα radiation. The crystal was mounted in a cryoloop under Paratone-N oil and cooled to 100 K with an Oxford-Diffraction Cryojet.

A complete sphere of data was collected using ω scans with 1° frame widths to a resolution of approximately 0.68 Å, equivalent to 2θ≈640. Reflections were recorded, indexed and corrected for absorption using the Oxford-Diffraction CrysAlisPro software, and subsequent structure determination and refinement was carried out using the single crystal x-ray structure refinement and analysis software package CRYSTALS, employing Superflip, a program for solution of crystal structures by charge flipping, to solve the crystal structure. All hydrogens were restrained to the connecting carbons. The refinement was performed against F2, with anisotropic thermal displacement parameters for all non-hydrogen atoms and with isotropic thermal displacement parameters for the hydrogens in the structure. A CIF was deposited with CCDC (No. 1550500).

Single Crystal x-Ray Diffraction Data and Collection Parameters.

The collection was performed at a temperature of 100 K.

| Compound | $[(CH_2)_6N_4]_3Pb_2Br_7$ |
|---|---|
| Formula | $C_{18}H_{36}N_{12}Pb_2Br_7$ |
| Molecular weight | 1394.29 g/mol |
| Space group | $P6_3/m$ (#176) |

-continued

| Compound | $[(CH_2)_6N_4]_3Pb_2Br_7$ |
|---|---|
| a | 24.5206 (4) Å |
| c | 9.7661 (2) Å |
| V | 5085.3 (2) Å$^3$ |
| Z | 6 |
| $\rho_{calc.}$ | 2.732 g/cm$^3$ |
| μ | 18.201 mm$^{-1}$ |
| Data collection range | 2.666° < θ < 32.095° |
| Reflections collected | 112162 |
| Independent reflections | 5272 |
| Parameters refined | 280 |
| Restraints | 108 |
| R$_1$, wR$_2$ | 0.0853$^a$, 0.0737$^b$ |
| Goodness-of-fit on F$^2$ | 1.1060 |

$^a R_1 = \Sigma ||F_o| - |F_c||/\Sigma |F_o|.$
$^b wR_2 = [\Sigma w(F_o^2 - F_c^2)^2/\Sigma w(F_o^2)^2]^{1/2}.$ Atomic Positions of $[(CH_2)_6N_4]_3Pb_2Br_7$.

All non-hydrogens were refined with anisotropic displacement parameters, while the hydrogens were refined with isotropic displacement parameters.

Pb—Br Bonds in $[(CH_2)_6N_4]_3Pb_2Br_7$

| Bond | Distance (Å) |
|---|---|
| Pb1—Br1 | 2.868 |
| Pb1—Br2 | 3.138 |
| Pb1—Br3 | 2.985 |
| Pb1—Br4 | 3.150 |
| Pb2—Br2 | 3.018 |
| Pb2—Br3 | 3.032 |
| Pb2—Br4 | 3.138 |
| Pb2—Br5 | 2.921 |

2. Powder X-Ray Diffraction (PXRD)

The PXRD analysis was performed on Panalytical X'PERT Pro Powder X-Ray Diffractometer using Copper X-ray tube (standard) radiation at a voltage of 40 kV and 40 mA, and X'Celerator RTMS detector. The diffraction pattern was scanned over the angular range of 5-50 degree (2θ) with a step size of 0.02, at room temperature. Simulated powder patterns were calculated by Mercury software using the crystallographic information file (CIF) from single-crystal x-ray experiment.

| Atom | Site | x | y | z | $U_{eq}$, $U_{iso}$ (Å$^2$) |
|---|---|---|---|---|---|
| Pb1 | 6h | 0.93868(3) | 0.65702(3) | 0.25 | 0.0242(3) |
| Pb2 | 6h | 1.13162(3) | 0.78579(4) | 0.25 | 0.0531(7) |
| Br1 | 6h | 0.90529(7) | 0.52701(6) | 0.25 | 0.0241(7) |
| Br2 | 12i | 0.86617(5) | 0.65139(5) | −0.01916(11) | 0.0329(6) |
| Br3 | 12i | 1.04247(5) | 0.68509(5) | 0.44732(9) | 0.0293(6) |
| Br4 | 6h | 1.01457(10) | 0.80536(8) | 0.25 | 0.044(12) |
| Br5 | 6h | 1.21604(9) | 0.73395(9) | 0.25 | 0.0463(10) |
| N11 | 12i | 0.6747(4) | 0.4578(4) | 0.1244(8) | 0.0281(5) |
| N12 | 6h | 0.6621(5) | 0.5361(6) | 0.25 | 0.0282(7) |
| N13 | 6h | 0.7657(6) | 0.5428(6) | 0.25 | 0.0322(8) |
| C14 | 12i | 0.6441(4) | 0.4949(5) | 0.1242(10) | 0.028(5) |
| C15 | 12i | 0.7439(4) | 0.5001(5) | 0.1286(10) | 0.028(5) |
| C16 | 6h | 0.6571(7) | 0.4204(7) | 0.25 | 0.0331(9) |
| C17 | 6h | 0.7355(6) | 0.5814(6) | 0.25 | 0.0276(8) |
| N21 | 12i | 0.9155(3) | 0.4749(3) | 0.6242(8) | 0.0217(4) |
| N22 | 6h | 0.8762(5) | 0.5338(6) | 0.75 | 0.0255(7) |
| N23 | 6h | 0.9884(5) | 0.5692(5) | 0.75 | 0.0232(6) |
| C24 | 12i | 0.8693(5) | 0.4947(5) | 0.6238(10) | 0.0299(6) |
| C25 | 12i | 0.9780(4) | 0.5296(4) | 0.6273(9) | 0.0213(5) |
| C26 | 6h | 0.9073(7) | 0.4364(7) | 0.75 | 0.0354(9) |
| C27 | 6h | 0.9416(7) | 0.5909(7) | 0.75 | 0.0316(9) |
| N31 | 12i | 1.1513(4) | 1.0250(5) | 0.1253(10) | 0.0465(6) |
| N32 | 6h | 1.2489(6) | 1.0591(7) | 0.25 | 0.0424(10) |
| N33 | 6h | 1.1681(7) | 0.9472(7) | 0.25 | 0.0427(9) |
| C34 | 12i | 1.2200(5) | 1.0692(5) | 0.1281(11) | 0.0352(6) |
| C35 | 12i | 1.1411(6) | 0.9616(6) | 0.1288(12) | 0.0462(8) |
| C36 | 6h | 1.1227(9) | 1.0350(11) | 0.25 | 0.0774(20) |
| C37 | 6h | 1.2354(8) | 0.9957(9) | 0.25 | 0.0512(13) |
| H141 | 12i | 0.6576(17) | 0.5220(14) | 0.045(3) | 0.033(2) |
| H142 | 12i | 0.5987(10) | 0.4673(13) | 0.124(4) | 0.033(2) |
| H151 | 12i | 0.7563(14) | 0.5257(14) | 0.048(2) | 0.033(2) |
| H152 | 12i | 0.7638(14) | 0.4745(14) | 0.131(4) | 0.033(2) |
| H161 | 6h | 0.678(2) | 0.3955(18) | 0.25 | 0.040(2) |
| H162 | 6h | 0.6120(12) | 0.3929(17) | 0.25 | 0.040(2) |
| H171 | 12i | 0.7483(11) | 0.6079(9) | 0.3313(15) | 0.0330(14) |
| H241 | 12i | 0.8753(17) | 0.5202(15) | 0.544(3) | 0.036(2) |
| H242 | 12i | 0.8273(11) | 0.4583(12) | 0.624(4) | 0.036(2) |
| H251 | 12i | 1.0087(12) | 0.5155(14) | 0.629(4) | 0.025(2) |
| H252 | 12i | 0.9847(15) | 0.5549(12) | 0.548(2) | 0.025(2) |
| H261 | 6h | 0.9376(19) | 0.4222(19) | 0.75 | 0.043(2) |
| H262 | 6h | 0.8651(14) | 0.4007(14) | 0.75 | 0.043(2) |
| H271 | 12i | 0.9474(12) | 0.6162(10) | 0.8314(15) | 0.0379(14) |
| H341 | 12i | 1.2274(15) | 1.1120(11) | 0.130(4) | 0.042(2) |
| H342 | 12i | 1.2387(13) | 1.0623(18) | 0.048(3) | 0.042(2) |
| H351 | 12i | 1.1602(19) | 0.9557(17) | 0.049(3) | 0.055(2) |
| H352 | 12i | 1.0961(12) | 0.9324(13) | 0.128(4) | 0.055(2) |
| H361 | 6h | 1.130(3) | 1.0777(18) | 0.25 | 0.094(2) |
| H362 | 6h | 1.0779(13) | 1.005(2) | 0.25 | 0.094(2) |
| H371 | 12i | 1.2544(12) | 0.9893(13) | 0.3313(15) | 0.0620(14) |

Figure 3:
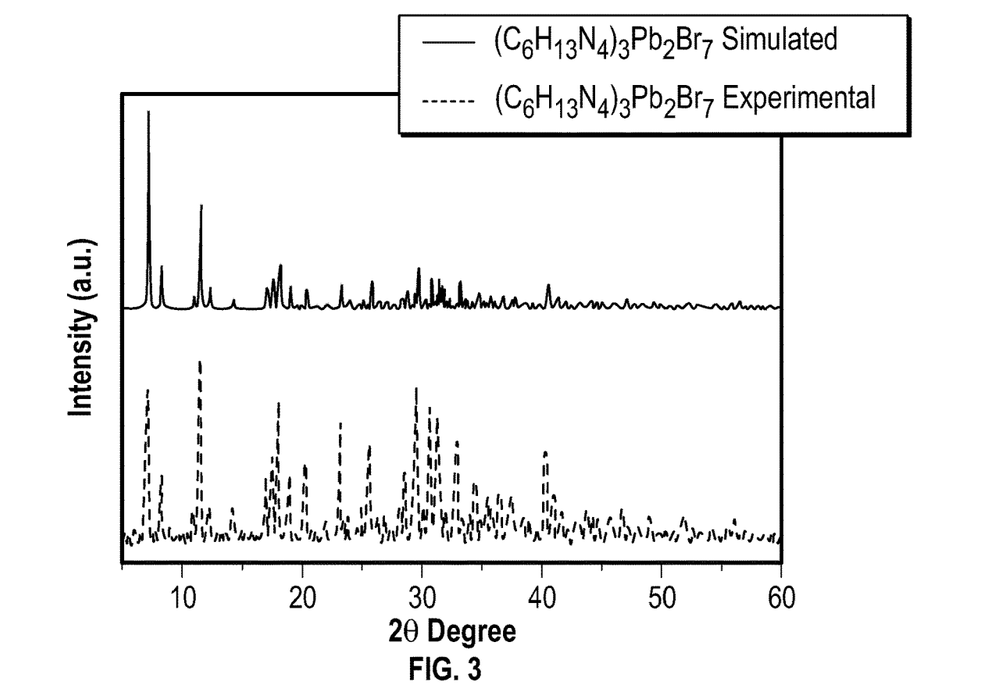
FIG. 3 depicts powder X-ray diffraction data of an embodiment of a bulk quantum material, as well as its simulated results.

FIG. 3 depicts PXRD data of the (HTMA)$_3$Pb$_2$Br$_7$ bulk quantum material of this example, as well as its simulated results. The powder X-ray diffraction (PXRD) pattern of the ball-milled sample was identical with the simulated PXRD pattern from the single crystal structure, which confirmed the SCXRD results.

3. Absorption Spectrum Measurements

Absorption spectra of bulk quantum materials were measured at room temperature through synchronous scan in an integrating sphere incorporated into the spectrofluorometer (FLS980, Edinburgh Instruments) while maintaining a 1 nm interval between the excitation and emission monochromators.

4. Excitation Spectrum Measurements

Excitation spectra of bulk quantum materials were measured at room temperature on a FLS980 spectrofluorometer (Edinburgh Instruments) monitored at maximum of emission spectra.

5. Photoluminescence Steady State Studies

Steady-state photoluminescence spectra of bulk quantum materials were obtained at room temperature and 77 K (liquid nitrogen was used to cool the samples) on a FLS980 spectrofluorometer.

6. Photoluminescence Quantum Efficiencies (PLQEs)

For photoluminescence quantum efficiency measurements, the samples were excited using light output from a housed 450 W Xe lamp passed through a single grating (1800 l/mm, 250 nm blaze) Czerny-Turner monochromator and finally a 5 nm bandwidth slit. Emission from the sample was passed through a single grating (1800 l/mm, 500 nm blaze) Czerny-Turner monochromator (5 nm bandwidth) and detected by a Peltier-cooled Hamamatsu R928 photomultiplier tube. The absolute quantum efficiencies were acquired using an integrating sphere incorporated into the FLS980 spectrofluorometer.

The PLQE was calculated by the equation: $\eta_{QE}=I_S/(E_R-E_S)$, in which $I_S$ represents the luminescence emission spectrum of the sample, $E_R$ is the spectrum of the excitation light from the empty integrated sphere (without the sample), and $E_S$ is the excitation spectrum for exciting the sample. Control samples, rhodamine 101 and blue phosphor BaMgAl$_{10}$O$_{17}$:Eu$^{2+}$, were measured using this method to give PLQEs of ~98% and ~93%, which were near the literature reported values. The PLQEs were double confirmed by a Hamamatsu C9920 system equipped with a xenon lamp, calibrated integrating sphere and model C10027 photonic multi-channel analyzer (PMA). The measurements took account of indirect PL provided the same results within the error bars.

7. Time-Resolved Photoluminescence

Time-Resolved Emission data were collected at room temperature and 77 K (liquid nitrogen was used to cool the samples) using time-correlated single photon counting on a Horiba JY Fluoromax-4 Fluorometer. Samples were excited with 365 nm pulsed diode lasers. Emission counts were monitored at 580 nm at room temperature and at 420, 480, 625 nm separately at 77K. The average lifetime was obtained by multiexponential fitting.

8. Materials Photostability Study

Figure 4:
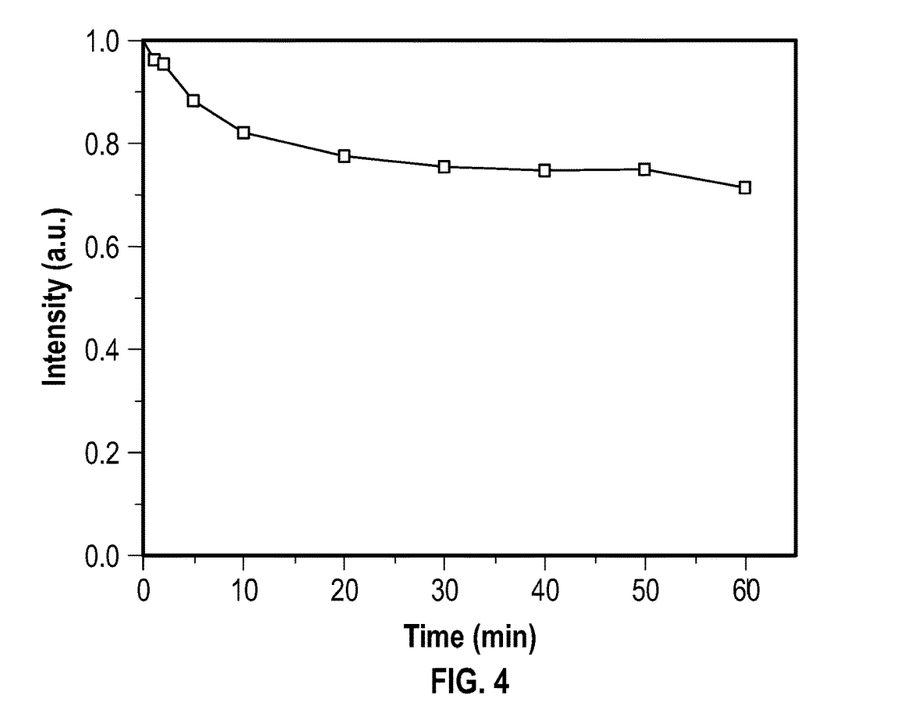
FIG. 4 depicts the photo-stability of an embodiment of a metal halide crystal having a 1D nanotube structure.

To test the photostability, a 100 W 20 V mercury short arc lamp was used as a continuous irradiation light source. The intensity of the irradiation was calibrated to 150 mW/cm$^2$. The emission was measured perodically on a HORIBA iHR320 spectrofluorimeter, equipped with a HORIBA Synapse CCD detection system. The results are depicted at FIG. 4.

The (HMTA)$_3$Pb$_2$Br$_7$ single crystals were observed and photographed under ambient light and UV light (365 nm). The colorless crystals emitted yellowish-white light or "warm" white under UV excitation with a reasonably good photostability, which suggested below-gap broadband emission with large Stokes shift.

Figure 5:
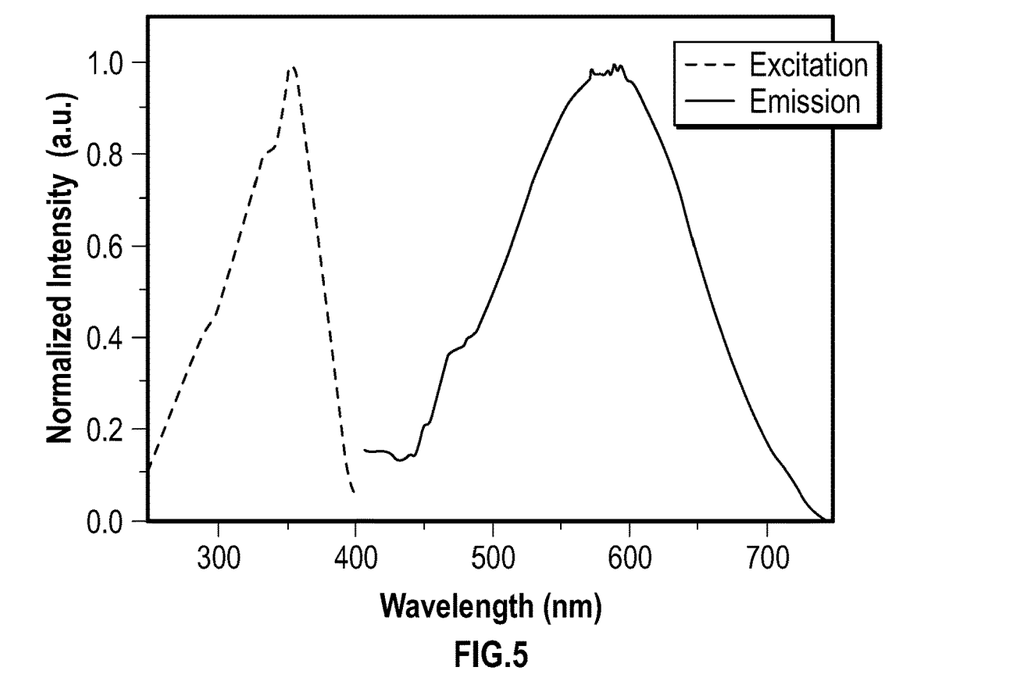
FIG. 5 depicts excitation (dash lines) and emission (solid lines, excited at 380 nm) spectra collected for an embodiment of a metal halide crystal having a 1D nanotube structure at room temperature.

FIG. 5 depicts excitation (dash lines) and emission (solid lines, excited at 380 nm) spectra collected for the (HMTA)$_3$Pb$_2$Br$_7$ crystals at room temperature. As shown at FIG. 5, (HMTA)$_3$Pb$_2$Br$_7$ was excited by UV light from 250 to 400 nm, and produced a broad emission peaked at 580 nm that covered a wide range of the spectrum from 450 to 750 nm, with a large FWHM of 158 nm.

The Comission Internationale de l'Eclairage (CIE) chromaticity coordinates for this yellowish-white emission were calculated to be (0.42, 0.45), which represented a significant red-shift, as compared to the bluish-white emission from the bulk assembly of 1D lead bromide nanowires (C$_4$N$_2$H$_{14}$PbBr$_4$) (Z. Yuan, et al., *Nat. Commun.* 2017, 8, 14051).

Figure 6:
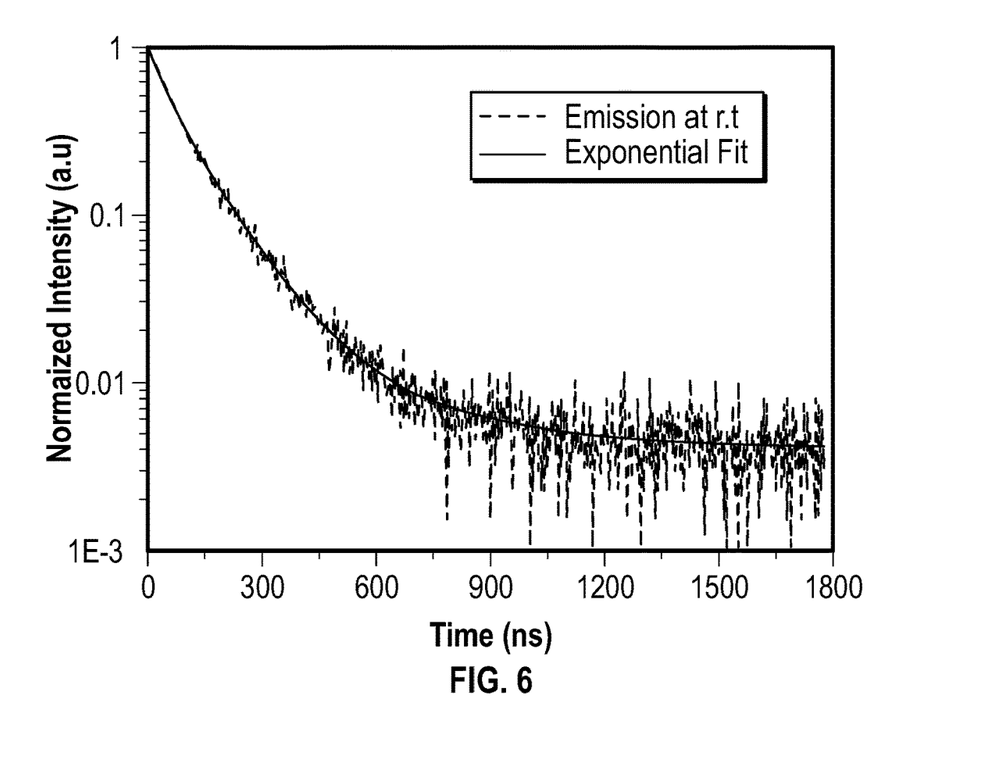
FIG. 6 depicts the emission decay of an embodiment of a metal halide crystal having a 1D nanotube structure (measured at 580 nm).

FIG. 6 depicts the emission decay of the (HMTA)$_3$Pb$_2$Br$_7$ crystals (measured at 580 nm) and fitting at room temperature. The emission decay was characterized by time-resolved photoluminescence spectroscopy. As depicted at FIG. 6, a multiple-exponential fitting of the intensity-time curve gave an average lifetime of approximately 127 ns. Such a strongly Stokes shifted broadband emission with relatively long lifetime was similar to what has been observed in corrugated-2D and 1D metal halide perovskites (see, e.g., Z. Yuan, et al., *Nat. Commun.* 2017, 8, 14051).

It was therefore reasonable to attribute this non-Gaussian shaped broadband emission to the self-trapped excited states with multiple energy minimums, which were in thermally activated equilibrium at room temperature. Unlike emissions from both free exciton and self-trapped excited states in bulk assembly of metal halide nanowires (C$_4$N$_2$H$_{14}$PbBr$_4$), only self-trapped emissions were recorded in (HMTA)$_3$Pb$_2$Br$_7$, which suggested the absence of delocalized excitonic states due to the ultrafast exciton self-trapping in (HMTA)$_3$Pb$_2$Br$_7$ at room temperature.

The electron coupling and molecular orbital interaction between the metal halide dimers via corner-sharing in 1D nanotubes likely were much weaker than those between 1D edge sharing metal halide octahedral nanowires. Therefore, the reduced conjugation in metal halide nanotubes likely produced more localized electronic states with stronger electron-phonon coupling, which favored the formation of self-trapped excitons.

Figure 7:
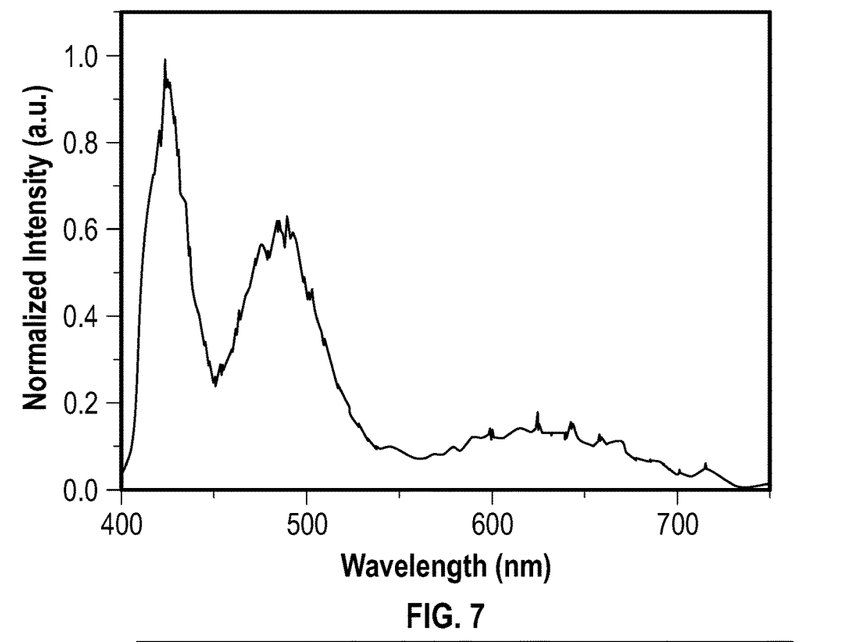
FIG. 7 depicts an emission spectrum of an embodiment of a metal halide crystal having a 1D nanotube structure (excited at 380 nm) at 77 K.

To further confirm the origin of broadband emission from self-trapped excited states, the photophysical properties of the (HMTA)$_3$Pb$_2$Br$_7$ crystals at 77 K were characterized, where thermally activated equilibrium was likely suspended. FIG. 7 depicts the emission spectra with three bands peaked at 420 nm, 480 nm and 625 nm.

Figure 8:
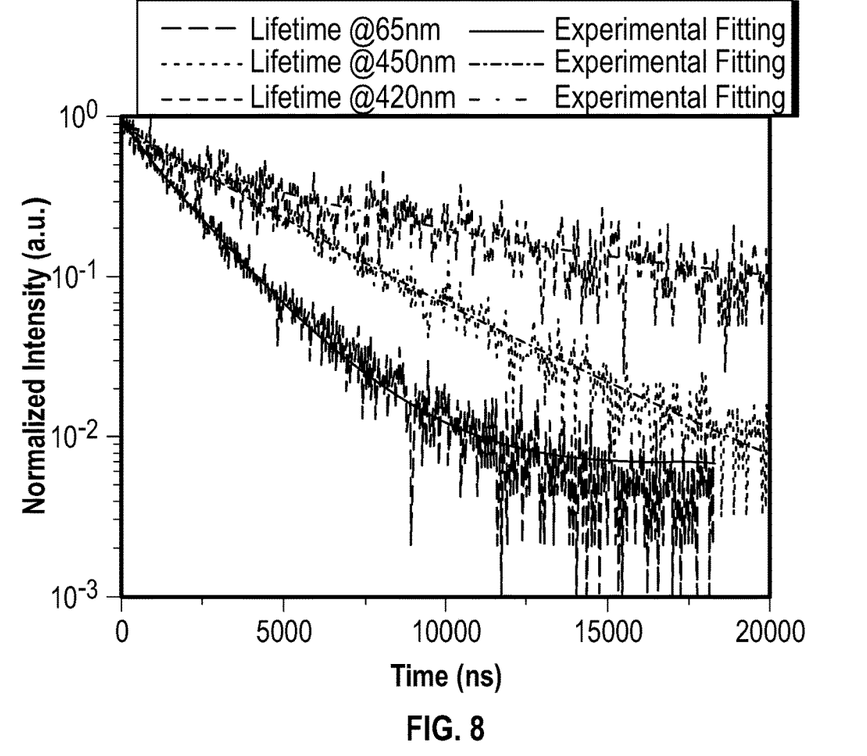
FIG. 8 depicts emission decays of the different emission peaks of FIG. 7 at 77 K.

FIG. 8 depicts the emission decays of the different emission peaks at 77 K and fittings for each curve. As depicted at FIG. 8, these emissions had different decay lifetimes, which were estimated to be 6.5 μs, 3.9 μs and 1.9 μs from short wavelength to long wavelength, respectively. Such distinct emission bands with different lifetimes at 77 K likely indicated multiple excited states generated upon photoexcitation, and were consistent with the inherent properties of exciton self-trapping in metal halide perovskites.

Figure 9:
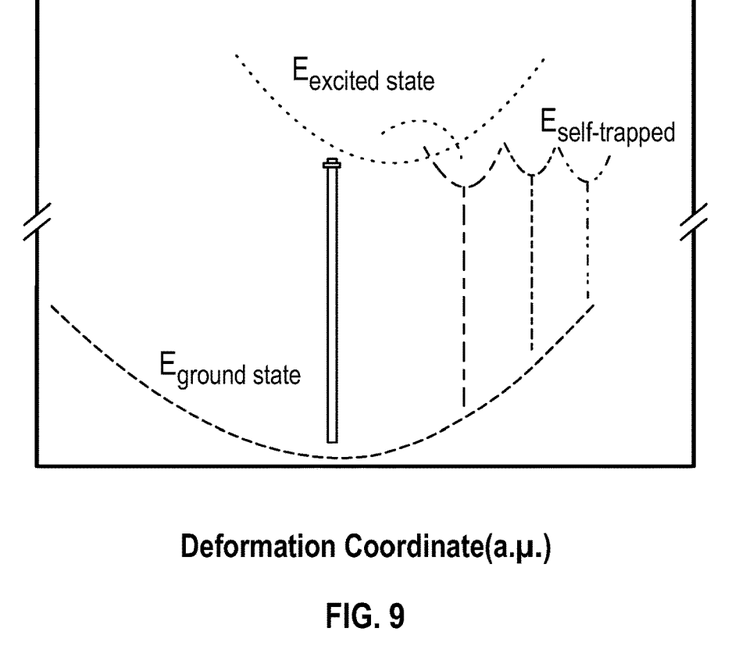
FIG. 9 depicts a proposed energy diagram and excited state dynamics of an embodiment of a metal halide crystal having a 1D nanotube structure (the straight and curved arrows represent optical and energy relaxation/transfer transitions, respectively).

Therefore, the photoluminescence mechanism for this bulk assembly of metal halide nanotubes can be depicted by the configuration coordinate diagram of FIG. 9. Upon UV excitation, the lead bromide nanotubes are excited to the high energy excited states, which undergo ultrafast exciton self-trapping with the formation of multiple excited states that give strongly Stokes shifted broadband photoluminescence at room temperature due to thermally activated equilibrium, and multiple emission bands at 77 K without thermally activated equilibrium. The observation of multiple exciton emission with strong temperature dependence resembles the emission of $ns^2$ ions in alkali halides (P. W. M. Jacobs, *J. Phys. Chem. Solids* 1991, 52, 35-67).

9. Thermogravimetry Analysis (TGA)

TGA was carried out using a TA instruments SDT: simultaneous DSC & TGA system of Q600 model. The samples were heated from room temperature (around 22° C.) to 800° C. at a rate of 10° C.·min$^{-1}$, under an argon flux of 100 mL·min$^{-1}$.

The hybrid material exhibited moderate thermal stability without decomposition up to around 155° C. in the TGA analysis.

10. Calculations

Density functional theory (DFT) calculations were performed.

Figure 10:
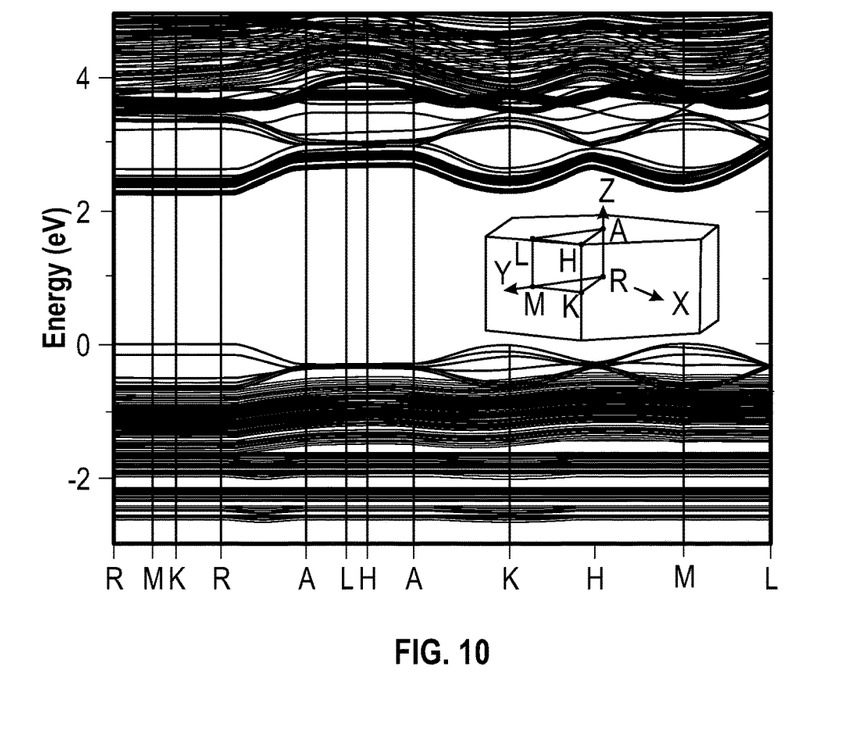
FIG. 10 depicts a calculated band structure of an embodiment of a metal halide crystal having a 1D nanotube structure.

The calculated band structure of $(HTMA)_3Pb_2Br_7$ (FIG. 10) showed a direct band gap at the Γ point.

The calculated band gap was 2.37 eV at the Perdew-Burke-Ernzerh (PBE) level, which was expected to be underestimated due to the well-known band gap error of DFT. The conduction and the valence bands were flat on the plane perpendicular to the axis of the $Pb_2Br_7$ tube, indicating negligible inter-tubular interaction. Along the axis of the tube, the band dispersion was still small, reflecting the weakened Pb—Br hybridization, likely due to the distortion of the $PbBr_6$ octahedral structure.

Figure 11:
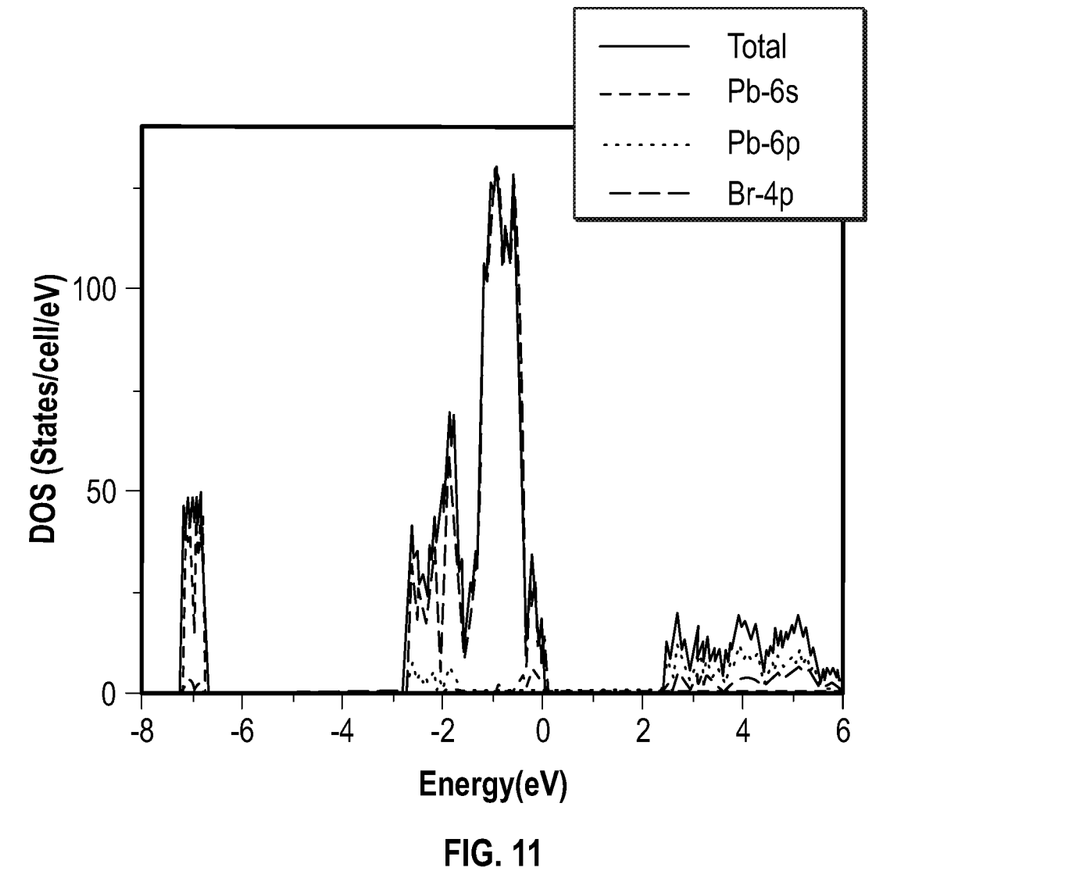
FIG. 11 depicts the projected density states of an embodiment of a metal halide crystal having a 1D nanotube structure.

The narrow bands near band edges and the soft lattice of $(HTMA)_3Pb_2Br_7$ should favor the charge localization and the formation of self-trapped excitons, consistent with the absence of free exciton emission at room temperature. The top of the valence band had significant Pb-6s character while the bottom of the conduction band was dominated by Pb-6p states, as shown by the projected DOS in FIG. 11. Thus, excitons should be localized on $Pb^{2+}$ ions and the emission was likely due to the Pb 6p-6s transition.

The calculations were based on density functional theory (DFT) implemented in the plane-wave basis VASP code (G. Kresse, J. Furthmüller, *Comput. Mater. Sci.*, 1996, 6, 15-50). The projector augmented wave method was used to describe the interaction between ions and electrons (G. Kresse, D. Joubert, *Phys. Rev. B* 1999, 59, 1758). Experimental lattice constants of hexagonal $(HTMA)_3Pb_2Br_7$ were used: a=24.5206 Å and c=9.7661 Å. Since the positions of the protons bonded to the HTMA molecules were not resolved experimentally, the organic cations were replaced by a uniform positive charge background such that the simulation cell was charge neutral.

This approximation did not affect the electronic structure near the valence and the conduction band edges because the electronic states derived from the organic molecules were far from the band gap (M. H. Du, *J. Mater. Chem. A* 2014, 2, 9091-9098; and T. Umebayashi, K. Asai, T. Kondo, A. Nakao, *Phys. Rev. B* 2003, 67, 155405). The kinetic energy cutoff of 216 eV and the 1×1×2 reciprocal space k-point mesh were used. The atomic positions were fully relaxed until the residual forces were less than 0.02 eV/Å. The band structure and the density of states (DOS) were calculated using the Perdew-Burke-Ernzerh (PBE) exchange-correlation functional (J. P. Perdew, K. Burke, M. Ernzerhof, *Phys. Rev. Lett.* 1996, 77, 3865). The spin-orbit coupling (SOC) was included in the calculations.

We claim:

1. A metal halide crystal comprising:
   a 1D nanotube structure, and
   a unit cell according to formula (I)—

$$R^d_a M^c_2 X_b \quad (I);$$

wherein R is an organic cation comprising at least one positively charged moiety,
   a is 2 to 8,
   M is a metal atom selected from the group consisting of Sn, Pb, Sb, Bi, Ag, Au, Pd, Pt, Mn, Fe, Co, Ni, Cu, and Zn,
   c is the charge of the metal atom,
   d is the charge of the organic cation,
   X is a halide ion selected from the group consisting of Cl, Br, and I,
   b is 5 to 12, and $$2(c)+a(d)=b.$$

2. The metal halide crystal of claim 1, wherein R comprises protonated hexamethylenetetramine (HMTA).

3. The metal halide crystal of claim 2, wherein d is 1.

4. The metal halide crystal of claim 1, wherein M is Pb.

5. The metal halide crystal of claim 1, wherein X is Br.

6. The metal halide crystal of claim 1, wherein R comprises protonated hexamethylenetetramine (HMTA), d is 1, a is 3, M is Pb, c is 2, X is Br, b is 7, and the unit cell of the metal halide crystal has the following formula:

$(C_6H_{13}N_4)_3Pb_2Br_7.$

7. The metal halide crystal of claim 6, wherein the metal halide crystal comprises six face-sharing lead bromide dimers of the formula $Pb_2Br_7^{3-}$.

8. The metal halide crystal of claim 1, wherein R is selected from the group consisting of— and a combination thereof.

9. The metal halide crystal of claim 1, wherein the metal halide crystal emits light in response to photo-excitation.

10. The metal halide crystal of claim 9, wherein the light emitted by the metal halide crystal is white light.

11. The metal halide crystal of claim 1, wherein the metal halide crystal has a photoluminescence quantum efficiency (PLQE) of about 7%.

12. The metal halide crystal of claim 1, wherein the 1D nanotube structure comprises a single-wall structure, a multiple-wall structure, or a combination thereof.

13. The metal halide crystal of claim 1, wherein the 1D nanotube structure comprises a metal halide tube having an inner portion and an outer portion, and the organic cations are located at (i) the inner portion of the metal halide tube, and (ii) the outer portion of the metal halide tube.

14. The metal halide crystal of claim 13, wherein a ratio of the number of organic cations located at the inner portion of the metal halide tube to the outer portion of the metal halide tube is about 1:2.

15. A method of making the metal halide crystal of claim 1 having a 1D nanotube structure, the method comprising:
   providing a liquid comprising a metal halide and an organic halide salt; and
   contacting the liquid with a crystallizing agent to form the metal halide crystal having a 1D nanotube structure;
   wherein the metal halide comprises a compound according to formula (II)—

$$MX_e \qquad (II);$$

wherein M is a metal atom selected from the group consisting of Sn, Pb, Sb, Bi, Ag, Au, Pd, Pt, Mn, Fe, Co, Ni, Cu, and Zn;
X is a halide ion selected from the group consisting of Cl, Br, and I; and
e is 1, 2, or 3.

16. The method of claim 15, wherein the liquid comprises dimethylformamide (DMF).

17. The method of claim 15, wherein M is Pb, X is Br, e is 2, and the metal halide has the following formula:

$$PbBr_2.$$

18. The method of claim 15, wherein the organic halide salt comprises hexamethylenetetramine hydrobromide.

19. The method of claim 15, wherein the crystallizing agent comprises dichloromethane.

20. A metal halide crystal comprising:
   a 1D nanotube structure, and
   a unit cell according to the following formula—

$$(C_6H_{13}N_4)_3Pb_2Br_7.$$

* * * * *